United States Patent [19]

Keith

[11] 4,456,587
[45] Jun. 26, 1984

[54] PHEROMONE DELIVERY SYSTEM

[75] Inventor: Alec D. Keith, Miami, Fla.

[73] Assignee: Key Pharmaceuticals, Inc., Miami, Fla.

[21] Appl. No.: 420,347

[22] Filed: Sep. 20, 1982

Related U.S. Application Data

[63] Continuation of Ser. No. 292,484, Aug. 13, 1981, abandoned, which is a continuation of Ser. No. 167,471, Jul. 11, 1980, abandoned, which is a continuation-in-part of Ser. No. 155,746, Jun. 2, 1980, abandoned.

[51] Int. Cl.³ .................. A01N 25/00; A61K 31/74
[52] U.S. Cl. ........................................ 424/78; 424/84
[58] Field of Search .................................... 424/78, 84

[56] References Cited

U.S. PATENT DOCUMENTS 4,210,633  7/1980  Takruri et al. ................... 424/28

FOREIGN PATENT DOCUMENTS 1046391    9/1956   Fed. Rep. of Germany .
47-27939   7/1972   Japan .
54-151117 11/1979   Japan .

OTHER PUBLICATIONS

Flint et al., J. Econ. Entomol. 67, 738–740, (1974).

Primary Examiner—Allen J. Robinson
Attorney, Agent, or Firm—Wegner & Bretschneider

[57] ABSTRACT

This invention provides an aqueous mixture capable of being sprayed onto the leaves of plants and being cured in situ on the leaves. The thus cured mixture comprises polyvinylalcohol and polyvinylpyrrolidone. The cured mixture is capable of the sustained release of an active ingredient contained therein.

3 Claims, No Drawings

PHEROMONE DELIVERY SYSTEM

CROSS-REFERENCE TO RELATED APPLICATION

This application is a continuation application of U.S. application Ser. No. 292,484, filed Aug. 13, 1981, which is in turn a continuation application of Ser. No. 167,471, filed July 11, 1980, which in turn is a continuation-in-part of my copending application Ser. No. 155,746, filed June 2, 1980, all abandoned.

DETAILED DESCRIPTION OF THE INVENTION

Pheromones are well known to be effective as attractants for insects. For such use a pheromone can be placed in an insect trap. In nature pheromones are present in very small quantity and effect mating between males and females of the same species. Pheromones may be mechanically dispersed on leaves of a crop plant to cause interference in the "normal" sexual behavior of a given insect species. For example, the insect pheromone Gossyplure (TM Zoecon, Palo Alto, Calif.) has been found to be effective in the treatment of cotton plants. For such treatment, the pheromone Gossyplure, has been found effective in treatments of cotton leaves to result in control of boll weevil populations on said cotton plants.

It is of considerable interest for agriculturalists to be able to control insect pests on important crop plants. The agriculturalist may need to control a variety of different insect pests on different crop plants. To effect such control the agriculturalists may want a pheromone to reside for a period of several weeks on plant leaves releasing the pheromone into the vapor phase and thus causing interference with a certain insects sexual behavior. The agriculturalist may also want to use traps containing a specific insect pheromone to result in trapping of said insect.

Gossyplure has been found effective in the control of the boll weevil on cotton plants. Applied alone or in simple solvent systems, gossyplure does not remain on the cotton leaves a sufficient time to be effective in the control of the boll weevil. In addition, Gossyplure is photosensitive and as a result is destroyed at a faster than usual rate by UV light.

In accordance with the present invention, a diffusion system based upon polyvinylalcohol and polyvinylpyrrolidone is provided which is sprayed onto the leafy surfaces of the leafy plant to be protected. Included in the spray mixture is the active ingredient, the pheromone, which is present in an effective amount to provide the desired protection over the period of larval activity of the insect.

In the case of Gossyplure as the pheromone, a suitable concentration per acre is 2.5 gm. If one uses 40 gallons as the amount of spray solution or dispersion to be applied per acre, the concentration of the active ingredient in the spray should preferably be at least about 2.5 gm per 40 gallons, although larger amounts may also be used, and with lesser total spray a higher concentration would be possible.

The combination of polyvinylalcohol and polyvinylpyrrolidone provides a polymeric spray which is "cast" directly onto the leafy surfaces of the leafy plants, e.g., cotton, and is "cured" generally within about 24 hours in situ on the leafy surfaces. If applied on a hot sunny day, the spray is relatively quickly dried, and curing is completed within a few hours. The thus-cured polymeric film containing minute quantities of the pheromone is fixed to the leafy surface and capable of remaining through the necessary treatment period, i.e., the mating stage of the particular species which may be, e.g. 4 to 6 weeks.

Since some materials suitable for spraying on plant leaves, including Gossyplure, are photosensitive it is sometimes beneficial to add a protective sunscreen in from 0.01 to 1% of the composition.

The combination of polymers has been found by applicant to provide in other systems a sustained release of materials contained therein. In the case of the very minute quantities of the pheromones, they are released in a sustained manner so that when the insect adults are on the leaf the minute quantities of pheromone necessary to interfere with the hormonal system of the insects are able to contact the pheromone receptors. In this manner, it is contemplated that a single application at the outset or slightly before the mating stage should protect the crop for the season. As the polymeric film contains the pheromone is should be expected that even with repeated rain that there should not be a need for reapplication of the spray treatment.

In a preferred embodiment, the polycinylalcohol has a molecular weight of from about 50,000 to about 150,000 and still more preferably from about 100,000 to about 150,000. As an example of a suitable polyvinylalcohol may be mentioned polyvinylalcohol is generally hydrolyzed to at least 90%, and preferably at least about 95%. The polyvinylpyrrolidone generally has a molecular weight of from about 15,000 to about 85,000, and preferably from about 20,000 to about 60,000, with 40,000 being an example of a more preferred embodiment. Generally there should be about 1.5 to 5 parts by weight of polyvinylalcohol per part polyvinylpyrrolidone. Optionally in a preferred embodiment glycerol is included in an amount up to about 10 parts per part polyvinylpyrrolidone.

The amount of water contained in the initial polymer mixture will vary dependent upon the amount of total spray to be applied per unit area and the dilution to be used for the spray to reach the amount of total spray. In one embodiment there is provided 12 gm polyvinylpyrrolidone to make up one pint of concentrated solution, which is then diluted with seven parts of water to yield a spray of the desired concentration to yield approximately 2.5 gm per acre, based upon 40 gallons spray per acre.

It is obviously to be understood that the specific amount of water is not critical within such ranges as will permit the interaction of the three polymeric components to yield a "cured" matrix on the leafy surfaces.

Generally included in the mixture will be an oil and a detergent. The pheromone is generally mixed into the oil, which may be, for example, a vegetable or mineral oil, and the oil containing the pheromone is then added to the polymeric mixture after the polymers have been thoroughly dispersed, which generally requires heating. Thus, the polymer components are added to the water, and generally heated to a temperature of at least about 90° C. to extend the polymers in the aqueous mixture. After cooling, the oil containing the active ingredient, the pheromone, is added, as well as the detergent. Minor amounts of both the oil and detergent are generally used, e.g., about one part each of oil and detergent per six parts polyvinylpyrrolidone, the exact amount of each of these ingredients not being critical.

The following examples illustrate the invention:

EXAMPLE I

The following ingredients are used:
10 gm polyvinylalcohol, mw 126,000, 96% hydrolyzed
5 gm polyvinylpyrrolidone, mw 40,000
5 gm glycerol
5 gm Tween 20 detergent
1 gm cottonseed oil
Balance water (balance=water to make up 125 ml).

The polyvinylalcohol, polyvinylpyrrolidone, and glycerol are added to the water, which is then mixed and heating occurs at a temperature of about 90° C. until the polymers have become extended into the mixture, after which the mixture is cooled to room temperature. 0.31 gm Gossyplure, a pheromone, is dispersed into the mineral oil, which together with the Tween 20 is then thoroughly mixed into the polymeric mixture, to yield one pint of concentrate. Prior to application, the concentrate is diluted with seven parts water to make up 1 liter, and applied through conventional aerosol techniques to the cotton plant leaves to protect the crop. The sprayed on polymeric mixture when applied on a sunny, hot day is cured in several hours.

EXAMPLE II

The procedure of Example I is followed, adding 0.3 gm of an alkylated derivative of a dihydroxy-4-methoxybenzophenone into the mixture concurrently with the cottonseed oil. (As a preferred dihydroxy-4-methoxybenzophenone may be mentioned UV-24 Spectra-sorb of American Cynamid Co.) The sunscreen effect of the added ingredient protects the pheromone from decomposition ordinarily caused by exposure to the sunlight.

Other examples of suitable sunscreen agents suitable for use with the present invention include polyvinylcinnamic acid, PABA, and polymerized PABA, and monomeric and polymeric analogs of PABA.

EXAMPLE III

In order to protect a tree from the encrouchment of insect growth, the composition of Example I is sprayed onto the bark of a tree, thereby providing protection against any insect that may come into contact with the tree. It will be understood that in place of the pheromone of Example I other insecticidally-effective ingredients may be substituted depending upon the nature of the insect problem being faced for the particular species of tree.

EXAMPLE IV

In place of the ingredients tabulated in Example I, there is used:
10 gm polyvinylalcohol, mw 126,000, 96% hydrolyzed
12 gm polyvinylpyrrolidone, mw 40,000
10 gm polyethylene glycol, mw 1000
2 gm Tween 20 detergent
2 gm mineral oil
Balance water (to make up one pint).

The ingredients are mixed together in the same manner as Example I and applied after seven-fold dilution to cotton crops. Although protection is obtained against the boll weevil the presence of the polyethylene glycol provides inferior results as compared with Example I, it being believed that this is due to the polyethylene glycol causing the sprayed and "cured" polymeric mixture to either not be affixed to the leaf or perhaps even causing separation from the leaf. Accordingly, although the mechanism may not be completely understood, it is contemplated that for any commercial operation, the inclusion of polyethylene glycol should be avoided.

What is claimed is:

1. An aqueous mixture for spraying onto the leaves of cotton plants consisting essentially of an amount of gossyplure effective to control the cotton boll weevil, polyvinyl pyrrolidone molecular weight from about 15,000 to about 85,000, 1.5 to 5 parts by weight per part polyvinyl pyrrolidone of polyvinyl alcohol molecular weight from about 50,000 to about 150,000, and up to about 10 parts by weight per part polyvinyl pyrrolidone of glycerol.

2. An aqueous mixture of claim 1 which includes mineral oil or a vegetable oil.

3. A method of applying gossyplure to the leafy surfaces of a cotton plant which comprises spraying onto said leafy surfaces an aqueous mixture consisting essentially of an amount of gossyplure effective to control the cotton boll weevil, polyvinyl pyrrolidone molecular weight from about 15,000 to about 85,000, 1.5 to 5 parts by weight per part polyvinyl pyrrolidone of polyvinyl alcohol molecular weight from about 50,000 to about 150,000, and up to 10 parts glycerol per part polyvinyl pyrrolidone, said aqueous mixture curing after application to said leafy surfaces and thereby retaining the gossyplure on said leafy surfaces.

* * * * *